Figure 1:
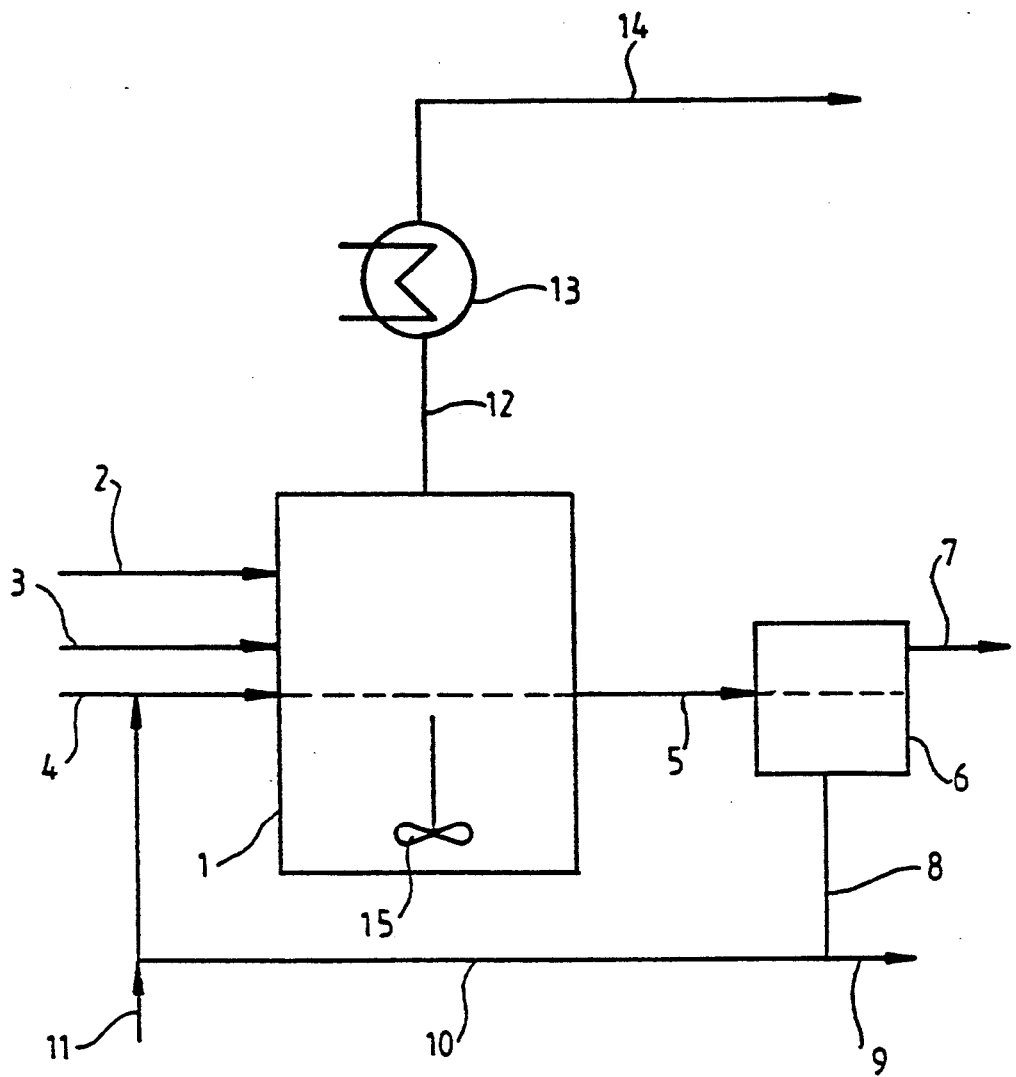

United States Patent [19]

Maass et al.

[11] Patent Number: 5,252,767
[45] Date of Patent: Oct. 12, 1993

[54] PROCESS FOR THE PREPARATION OF ORGANOSILOXANES

[75] Inventors: Günther Maass, Gladbach; Manfred Schulze, Leichlingen, both of Fed. Rep. of Germany

[73] Assignee: Bayer Aktiengesellschaft, Leverkusen, Fed. Rep. of Germany

[21] Appl. No.: 915,160

[22] Filed: Jul. 16, 1992

[30] Foreign Application Priority Data

Jul. 26, 1991 [DE] Fed. Rep. of Germany ........ 4124802

[51] Int. Cl.$^5$ ................................................ C07F 7/08
[52] U.S. Cl. ...................................... 556/450; 556/460
[58] Field of Search ............................... 556/460, 450

[56] References Cited

U.S. PATENT DOCUMENTS

| | | | |
|---|---|---|---|
| 4,032,557 | 6/1977 | Spork et al. | 260/448.2 E |
| 4,222,953 | 9/1980 | Mahone | 556/460 X |
| 4,366,324 | 12/1982 | Habata et al. | 556/460 |
| 4,609,752 | 9/1986 | Giesing et al. | 556/457 |

FOREIGN PATENT DOCUMENTS

| | | |
|---|---|---|
| 0167924 | 1/1986 | European Pat. Off. . |
| 2521742 | 11/1976 | Fed. Rep. of Germany . |
| 3202558 | 8/1983 | Fed. Rep. of Germany . |
| 2087915 | 6/1982 | United Kingdom . |

*Primary Examiner*—Paul F. Shaver
*Attorney, Agent, or Firm*—Sprung Horn Kramer & Woods

[57] ABSTRACT

This invention relates to a process for the preparation of organosiloxanes, in particular those containing a high proportion of low molecular weight cyclic and chain structured organosiloxanes, preferably cyclic dimethylsiloxanes, by hydrolysis of the corresponding organochlorosilanes, in which a high proportion of gaseous hydrogen chloride is formed at the same time.

9 Claims, 1 Drawing Sheet

PROCESS FOR THE PREPARATION OF ORGANOSILOXANES

This invention relates to a process for the preparation of organosiloxanes, in particular those containing a high proportion of low molecular weight cyclic and chain structured organosiloxanes, preferably cyclic dimethylsiloxanes, by hydrolysis of the corresponding organochlorosilanes, in which a high proportion of gaseous hydrogen chloride is formed at the same time.

Organosiloxanes are important preliminary products of silicone chemistry. The organosiloxanes are generally obtained by the hydrolysis of organochlorosilanes. Hydrolysis takes place via the intermediate stage of the formation of organosilanols with the splitting off of hydrogen chloride. Silanol groups are highly reactive under acid conditions and enter into secondary reactions with SiCl or SiOH groups to form the characteristic siloxane groups (Si—O—Si) of silicones. When diorganodichlorosilanes are used, the formation of cyclic diorganosiloxanes is accompanied by the formation of chain structured α,ω-dihydroxypolydiorganosiloxanes which leads to the synthesis of higher molecular weight organosiloxanes. Branched organosiloxanes are formed when organotrichlorosilanes are used, hexaorganodisiloxanes are formed when triorganomonochlorosilanes are used and the use of mixed silanes leads to the formation of mixed forms of the above-mentioned organosiloxanes.

Owing to the high viscosity of the relatively high molecular weight organosiloxanes, their presence is undesirable in subsequent processing steps such as purification, distillation, etc. There has therefore been no lack of attempts to increase the proportion of low molecular weight organosiloxanes in the product of hydrolysis.

Thus the content of cyclic products in the hydrolysate of diorganodichlorosilanes can be increased to 95% by the addition of surface-active substances (U.S. Pat. No. 3,983,148, U.S. Pat. No. 4,412,080, U.S. Pat. No. 4,423,240, U.S. Pat. No. 4,447,630). These methods, however, are unsatisfactory because of the effort required for the subsequent removal of the surface-active substances from the siloxane mixture since impurities in amounts of only about 1 ppm are sufficient to cause subsequent degradation of the polyorganosiloxane end products.

Other methods for the preparation of organosiloxanes use organochlorosilanes and methanol as starting material with the aim of converting them into organosiloxane and methyl chloride (methanolysis). Methyl chloride may be used directly in the Rochow synthesis for the reaction with metallic silicon to form methyl chlorosilanes. The reaction of organochlorosilanes with methanol to form organosiloxanes and methyl chloride, however, proceeds relatively slowly so that only an unsatisfactory volume/time yield is obtained. It was therefore aimed to develop suitable catalysts (DE-A 2 557 624) for the formation of methyl chloride but the yields still remained less than the yields from the hydrolysis reaction by a factor of 3–4 so that no advantage was obtained from the simultaneous preparation of methyl chloride and siloxanes. Moreover, methanolysis always leads to the formation of aqueous hydrochloric acid which must be disposed of.

It is a primary object of the present invention to provide a process by which organosiloxanes containing more than 75% by weight, preferably more than 85% by weight of low molecular weight organosiloxanes can be obtained and in which the disadvantages of the process of methanolysis are avoided.

From a process technical point of view, the process according to the invention belongs to the class of processes which are carried out with an installation shown in FIG. 1. The process technical layout of the process according to the invention will first be described with reference to FIG. 1. The reagents are first introduced into a hydrolysis reactor 1 from one or more pipes 2, 3, 4. A stirrer 15 for mixing the reagents may be provided in the reactor 1. The reactor liquid is transferred along a pipe 5 to a phase separator 6 in which the reactor liquid composed of two phases differing in density can separate into an upper phase and a lower phase. The hydrolysate consisting of the organosiloxanes is removed through a pipe 7 which is connected to the phase separator 6 above the phase boundary surface and the hydrolysate may be transferred to a stage of purification for removing residues still adhering to it from the lower phase separated in the phase separator. The lower phase, containing mainly all the other components of the reactor liquid apart from the hydrolysate, is removed from the phase separator via pipe 8. This lower phase may either be discharged from the process through pipe 9 without further treatment or returned to the hydrolysis reactor through pipe 10. Gaseous products of hydrolysis are removed through pipe 12 above the hydrolysis reactor to enter a reflux condenser 13 where they are freed from condensable components which are returned to the hydrolysis reactor. The gaseous products of hydrolysis freed from condensable components are removed from the reflux condenser along pipe 14 for further use.

The process according to the invention also belongs to the class of processes in which the conversion of organochlorosilanes to organosiloxanes is carried out in the presence of water, methyl alcohol and hydrochloric acid and in the absence of catalysts which favour the formation of cyclic compounds.

It has now been found that the hydrolysate will contain particularly high proportions of low molecular weight organosiloxanes if certain methanol levels are maintained in the reactor liquid. In a general characterisation of the process according to the invention, this is characterised in that the lower phase, which is separated in the phase separator and consists mainly of water, hydrochloric acid and methanol, contains a molar proportion of water to methanol of from 0.3 to 10. The molar ratio is preferably above 0.6, most preferably above 0.9. The upper limit for the molar ratio is preferably 3, more preferably 1.8 and most preferably 1.2.

The starting materials used according to the invention are in particular diorganodichlorosiloxanes, which give rise to a high proportion of cyclic diorganosiloxanes. The preferred diorganodichlorosilane is dimethyldichlorosilane.

The invention is described below with the aid of an example using dimethyldichlorosilane. The description is, of course, equally applicable to the hydrolysis of other organosilanes.

According to the invention, therefore,, the supply of dimethyldichlorosilane, water and methanol through pipes 2, 3 and 4 of FIG. 1 should be so controlled that the liquid leaving the phase separator through pipe 8 has the ratio of water and methanol which characterises the invention.

It is preferred according to the invention to limit the average residence time in the reactor to below 30 minutes. By average residence time is meant the total quantity of reagents supplied per hour through pipes 2, 3 and 4 divided by the volume of liquid in the hydrolysis reactor. If, therefore, the outflow pipe 5 of the hydrolysis reactor is arranged as overflow in the usual manner, the liquid level in the hydrolysis reactor is situated at the level of the mouth of the overflow pipe 5.

According to the invention, the temperature in the hydrolysis reactor is maintained at 40° to 90° C. Temperatures up to 120° C. are no disadvantage with regard to the yield of cyclic organosiloxanes but higher temperatures up to 120° C. favour the formation of methyl chloride, which is discharged from the process through pipe 14 together with the uncondensable gaseous components. If, however, the gas discharged through pipe 14, which consists mainly of hydrogen chloride, is required to be subsequently converted into methyl chloride for further use in the Rochow synthesis, it may be desirable to increase the proportion of methyl chloride in the gaseous product of hydrolysis in order to reduce the amount of work in the reactor subsequently used for the reaction of hydrochloric acid and methanol to form methyl chloride. For process technical reasons of the operation of the hydrolysis reactor, however, it is preferred not to use excessively high temperatures. Temperatures from 50° to 80° C. are particularly preferred as these are particularly suitable for the degasification of hydrogen chloride.

The hydrolysis reactor may be at normal gas pressure but the process may equally well be carried out under a slight vacuum. A slight excess pressure, however, is generally preferred as this promotes the transport of the gaseous products of hydrolysis through pipe 14. When the process according to the invention is carried out on a large technical scale, an excess pressure of about 1 bar is advantageously employed as this excess pressure assists the transport through pipes 14 to the subsequent apparatus without the aid of pumps. A further increase of pressure of up to 2 bar may also be advantageous for reducing the volume of gas bubbles in the hydrolysis liquid.

Vigorous mixing of the liquid phases should be ensured in the reaction vessel. Various apparatus known in the art may be used as mixing apparatus, e.g. a stirrer vessel equipped with a vigorous stirrer with baffles, a column containing any of various installations or filling bodies, a static mixer with adjacent pacifying zone, etc. Whatever arrangement is chosen, the possibility of phase separation after the reaction must be provided both for the gas-liquid region and for the oily, aqueous and liquid phases.

The temperature in the hydrolysis reactor may be controlled by adjustable external heating means if the dimethyldichlorosilane is supplied in the liquid form at about room temperature but the dimethyldichlorosilane may equally well be introduced in the gaseous form into the bottom of the hydrolysis reactor after it has been evaporated at an elevated temperature, and may thus be used for the temperature control. If the dimethyldichlorosilane is supplied in gaseous form, care must be taken to ensure that it is introduced in the form of sufficiently small bubbles into the hydrolysis reactor so that the bubbles will not pass through the surface of the hydrolysis liquid to be discharged from the reactor with the gaseous products of hydrolysis. For process technical reasons it appears simplest to introduce the dimethyldichlorosilane in liquid form into the hydrolysis reactor, either from below the liquid level or by free fall through the gas space above the liquid level.

The reaction may also be carried out by introducing the reactants in a gaseous form into the gas space above the hydrolysis liquid so that hydrolysis takes place mainly in the gas space and the condensable products of hydrolysis condense in the reflux condenser and are returned to the hydrolysis reactor. This method of reaction is less advantageous from an energy point of view but provides higher volume/time yields since there is virtually no degasification of the liquid volume.

It has also been found that the amount of methanol required according to the invention in the lower phase, which is removed from the phase reactor, may be maintained by introducing water and methanol into the hydrolysis reactor in a total quantity of at least one mol per equivalent of the chlorine directly attached to silicon in the organo-chlorosilane supplied and by ensuring that the molar ratio of water and methanol supplied still amounts to 0.3 to 10, preferably 0.9 to 1.8, after the removal of 0.5 mol of water per equivalent of the chlorine directly attached to silicon in the organochlorosilane. The present experimental finding appears to indicate that in the ideal case according to the invention a molar ratio of water to methyl alcohol of about 0.9 to 1.2 after removal of 0.5 mol of water used for the hydrolysis reaction provides optimum conditions.

According to the invention, the lower phase leaving the phase separator is preferably at least partly returned to the hydrolysis reactor. The supply of fresh water and methyl alcohol may then be reduced by the amount returned.

If the reactor is in the form of a simple stirrer vessel, the process according to the invention enables a yield of at least about 800 g of organosiloxanes to be obtained per liter of reactor volume (liquid filling) and hour. The yield of cyclic dimethylsiloxanes is at least 560 g per liter of reactor volume (liquid filling) and hour. Up to 2000 g of organosiloxanes have been obtained per liter of reactor volume.

The limiting factor for the volume/time yield is the separation of the gaseous products of hydrolysis. An increase to 2 to 3 times the volume/time yield can easily be obtained according to the invention by using reactors which are specially designed for degasification processes. According to the invention., however, a simple, enamel lined stirrer vessel is preferred owing to the low process technical expense involved, even if the optimum volume/time yield is then not obtained.

In one (particularly preferred) embodiment of the process according to the invention, substantially 100% of the hydrochloric acid theoretically obtainable from the dimethyldichlorosilanes can be obtained in the form of a gaseous product of hydrolysis. In this particularly preferred embodiment of the process according to the invention, 100% of the lower phase obtained from the phase separator is returned to the hydrolysis reactor and the amount of water returned to the hydrolysis reactor is then only about 0.5 mol per equivalent of the chlorine directly attached to silicon in the dimethyl-dichlorosilane. In fact, however, slightly larger quantities of water and in addition small quantities of methanol must be supplied because the gaseous hydrogen chloride discharged still contains small quantities of methyl chloride and because the amounts of water and methanol which have been lost due to being discharged with the hydrolysate must be replaced. A particularly preferred process according to the invention is therefore one in which only 0.5 to 0.55 mol of water are introduced into the hydrolysis reactor per equivalent of the chlorine directly attached to silicon in the organochlorosilane and the lower phase obtained in the phase separator is completely returned and in which, further, methanol is added only in the amount equal to the methanol discharged from the circulation in the form of methyl chloride and of methanol adhering to the upper phase. According to the invention, therefore, the circulation composed of hydrolysis reactor and the lower phase of the phase separator is most preferably only supplied with organochlorosilane, 0.5 to 0.55 mol of water per chlorine directly attached to silicon in the organochlorosilane and 0.001 to 0.1 mol, preferably up to 0.05 mol, of methanol per chlorine directly attached to silicon in the organochlorosilane.

According to the invention, the methanol takes part in the hydrolysis reaction only as an intermediary without itself forming reaction products. It is evident that according to the invention methanol acts as catalyst or catalytic reaction medium which promotes the formation of cyclic products and the formation of low molecular weight organosiloxanes.

This preferred process according to the invention, which enables at least 75% of the theoretical yield from the organochlorosilane to be obtained as gaseous hydrogen chloride, also enables the yield of organosiloxanes to be increased to about 1200–2000 g/l of reactor volume (liquid filling) and hour. The yield of cyclic dimethylsiloxanes is at least 950 g per liter of reactor volume (liquid filling) and hour. The above-described steady state of the process according to the invention can be arranged at the start of the reaction by introducing into the hydrolysis reactor a liquid consisting of 3 parts of water and 1 part of methanol (molar) and then supplying the above-mentioned strict ratios of organochlorosilane, water and methanol in such a quantity that the average residence time as defined above is from about 5 minutes to 30 minutes.

Until equilibrium is established, the rate of addition of methanol may have to be varied according to the results of analysis of the lower phase leaving the phase separator in order that the state of equilibrium for the continuous process may be obtained more quickly.

In long term tests carried out on the particularly preferred embodiment of the process according to the invention, no interference of the process by any by-products formed was detected. Apart from minor proportions of methyl chloride in the gaseous product of hydrolysis, no amounts of dimethylether which could interfere with the process was found. This is presumably due to the comparatively high concentration of HCl in the hydrolysis reactor.

The water required for the process may be supplied in the form of aqueous hydrochloric acid. For example, a hydrochloric acid which is at a lower concentration than in an azeotropic composition and which was used for washing the hydrolysate to remove components adhering to it from the lower phase of the phase separator and which in addition contains components from the hydrolysis reactor, may advantageously be used for supplying the water required for hydrolysis. The additional quantity of hydrochloric acid thereby introduced into the hydrolysis reactor may then be obtained as an additional amount of gaseous hydrogen chloride. By these means, even up to 120% of the quantity of hydrogen chloride theoretically obtainable from the organohalogensilane put into the process can be discharged from the process in the form of gaseous hydrogen chloride via pipe 14 of FIG. 1, i.e. this proportion of aqueous hydrochloric acid may be dehydrated to yield gaseous hydrogen chloride.

In view of the high volume/time yields which are preferably obtained according to the invention, with about 80% of cyclic dimethylsiloxanes, with quantitative return of the lower phase from the phase separator and quantitative recovery of the chlorine in the form of gaseous hydrogen chloride, it would appear that the previous aims of technology to carry out methanolysis, which favours the formation of cyclic products, with a view to obtaining methyl chloride at the same time in only one reactor have led along a path of development which has hindered the discovery of the catalytic effect of methanol for hydrolysis. Methanolysis of organochlorosilanes accompanied by the formation of methyl chloride as such is a water-releasing process which is inevitably accompanied by the formation of aqueous hydrochloric acid which cannot easily be put to good use. It is only the discovery that the hydrolysis reaction can under certain conditions be carried out successfully in the presence of methanol without the aim of producing products from methanol that has turned attention away from this technological line of development.

The invention will now be explained in more detail with the aid of the following Examples which, however, should not limit their general character.

EXAMPLE 1–5

The reaction vessel used was a 2-liter four-necked flask equipped with two intensive reflux condensers arranged in series, a glass stirrer a contact thermometer and a short inlet tube with two inlets. An overflow tube arranged at half the height of the flask (liquid volume 1 liter) leads via a submerged feed pipe to a 0.5-liter, horizontally placed separating flask having an outflow for the lower phase and an outflow for the upper phase. The contact thermometer is connected by a relay to a heating mushroom which covers the lower half of the flask. The water cooled intensive reflux condensers are connected by a gas discharge pipe to a 2-liter two-necked flask on one neck of which is seated a column of filling bodies 80 cm in length and 3 cm in diameter. Water is trickled into the column of filling bodies from above for absorbing the gas produced. The water is able to flow into a receiver from the bottom of the 1-liter flask via a submersed feed pipe. The nature and quantity of gas produced is thus determined in the aqueous phase. The upper end of the column is ventilated for safety's sake by means of a tube with two safety washing bottles. Each of the two inlets at the short inlet tube of the reaction vessel is connected to a laboratory metering puma via a Teflon tube. The intake side of each pump is connected to a storage vessel for dimelhyldichlorosilane or hydrochloric acid/methanol/water mixtures via a Teflon tube with intake suction tube.

The reactor was first filled with the quantity of methanol/water or methanol/hydrochloric acid/water mixture shown in Table 1. The mixture and dimethyldichlorosilane were then dosed in the quantities shown in Table 1. The temperature was kept constant as indicated in Table 1. Equilibrium was established after about 2 hours.

The upper phase was washed with water immediately after being discharged and was then mixed with 2% sodium hydroxide solution. After separation of the sodium hydroxide solution, the viscosity of the silicone oil was determined, as shown in Table 2. The last but one column of Table 2 shows the yield of cyclic dimethylsiloxanes (n=3–8) in g/h and per liter of reactor volume (liquid filling) and the percentage yield of the total quantity of silicone oil obtained. The Table also shows the analyses of the gaseous products streams,, the lower phase and the hydrochloric acid contents of the upper phase, both in g/h (upper figure) and in mol/h (lower figure).

TABLE 1

| Example No. | to the reactor $ME_2SiCl_2$ | $H_2O$ | MeOH | HCl | T °C. | t min l/kg |
|---|---|---|---|---|---|---|
| 1 | 1370 | 737 | 872 | — | 90 | 20.1 |
|   | 10.6 | 40.9 | 27.2 | — |    |      |
| 2 | 1369 | 742 | 889 | 297 | 63 | 18.2 |
|   | 10.6 | 41.2 | 27.8 | 8.1 |    |      |
| 3 | 2602 | 565 | 361 | 188 | 55 | 16.1 |
|   | 20.2 | 31.4 | 11.3 | 5.2 |    |      |
| 4 | 2025 | 432 | 300 | 253 | 60 | 19.8 |
|   | 15.7 | 24 | 9.4 | 6.9 |    |      |
| 5 | 1417 | 298 | 174 | 268 | 65 | 27.8 |
|   | 11 | 16.5 | 5.4 | 7.3 |    |      |

TABLE 2

| Ex. No. | Gas | | Lower phase | | | Upper phase | | | Yield $(Me_2SiO)_n$ g/h · l | Viscosity Silicone oil mPa · s |
|---|---|---|---|---|---|---|---|---|---|---|
|   | HCl | MeCl | HCl | MeOH | $H_2O$ | total | HCl | $(Me_2SiO)_n$ |   |   |
| 1 | 201 | 24 | 528 | 848 | 566 | 774.7 | 24.8 | 565 | 565 | 8.2 |
|   | 5.5 | 0.5 | 14.5 | 26.5 | 31.4 |   | 0.68 | 7.6 | 73% |   |
| 2 | 290 | 2.7 | 749 | 883 | 541 | 824 | 28.8 | 640 | 640 | 6.4 |
|   | 7.9 | 0.05 | 20.5 | 27.6 | 30 |   | 0.8 | 8.6 | 80.5% |   |
| 3 | 1282 | 43 | 283 | 328 | 171 | 1597 | 67 | 1348 | 1348 | 5.9 |
|   | 35 | 0.85 | 7.8 | 10.2 | 9.5 |   | 1.8 | 18.2 | 88.1% |   |
| 4 | 1100 | 37.3 | 227 | 275.2 | 145 | 1197 | 42 | 960 | 960 | 6.1 |
|   | 30.2 | 0.74 | 6.2 | 8.6 | 8.1 |   | 1.15 | 12.9 | 83.1% |   |
| 5 | 864 | 49.5 | 131 | 141 | 100 | 843 | 35.4 | 660 | 660 | 6.6 |
|   | 23.7 | 0.98 | 3.6 | 4.4 | 5.5 |   | 0.97 | 8.9 | 81.8% |   |

EXAMPLE 6

The same apparatus as in Examples 1 to 5 was used but the lower phase leaving the separating flask was directly returned to the reactor. To start the reactor, a mixture of 300 g of methanol, 300 g of HCl and 300 g of $H_2O$ was introduced. 2220 g of dimethyldichlorosilane (17 mol), 310 g of water (17.2 mol) and an average of 27 g of methanol (0.85 mol) were then introduced continuously per hour. The temperature of the reactor was maintained at 58° C. Constant conditions were established after 2 hours.

1300 g of liquid were separated hourly as upper phase. The liquid contained 45 g of hydrochloric acid and 1250 g of silicones having a viscosity of 6.0 mPa.s. The proportion of cyclic silicones was 84.5%. The gaseous phase contained 1665 g of HCl gas (32 mol) corresponding to 94% of the amount of hydrochloric acid theoretically obtainable from the dimethyldichlorosilane, and 40 g of methyl chloride. The reaction was stopped after a continuous operation of 10 days without any negative effects.

EXAMPLE 7

The procedure was the same as in Example 6 but 390 g of 20% hydrochloric acid obtained from washing the silicone product were supplied instead of water. With otherwise substantially unchanged product data, the gaseous phase obtained contained 1245 g of HCl gas (34 mol).

We claim:
1. A process for the preparation of organosiloxanes and gaseous hydrogen chloride by the hydrolysis of organochlorosilanes in a hydrolysis reactor and separation of the product organosiloxane from the hydrolysis liquid by phase separation, characterised in that hydrolysis is carried out in the presence of methanol.

2. A process according to claim 1, characterised in that the aqueous phase separated from the organosiloxane product in the phase separator has a molar ratio of water to methanol of from 0.3 to 10.

3. A process according to claim 1, characterised in that organochlorosilane, water and methyl alcohol are supplied to the hydrolysis reactor, the molar ratio of water and methyl alcohol supplied still amounting to a value from 0.3 to 10 in the reaction mixture after the removal of 0.5 mol of water per equivalent of chlorine attached to silicon in the organochlorosilane introduced.

4. A process according to one of the claim 1, characterised in that water and methyl alcohol are added in a total quantity of at least 1 mol per equivalent of the chlorine directly attached to silicon in the organochlorosilane introduced.

5. A process according to one of the claim 1, characterised in that water and methyl alcohol are supplied in a total quantity of not more than 1.15 mol per equivalent of the chlorine directly attached to silicon in the organosilane supplied.

6. A process according to one of the claim 1, characterised in that the lower phase from the separation of the organosiloxane product is returned to the hydrolysis reactor.

7. A process according to claim 6, characterised in that in addition to the lower phase, which is returned, from 0.5 to 0.55 mol of water and from 0.001 to 0.1 mol of methyl alcohol are supplied per equivalent of the chlorine directly attached to silicon in the organochlorosilane.

8. A process according to claim 7, characterised in that the water is supplied in the form of aqueous hydrochloric acid.

9. A process according to one of the claim 1, characterised in that the average residence time in the hydrolysis reactor is from 5 to 30 minutes.

* * * * *

UNITED STATES PATENT AND TRADEMARK OFFICE
CERTIFICATE OF CORRECTION

PATENT NO. : 5,252,767
DATED     : October 12, 1993
INVENTOR(S): Maass, et al.

It is certified that error appears in the above-indentified patent and that said Letters Patent is hereby corrected as shown below:

Col. 8, line 24    Delete " one of the "

Col. 8, line 43    Delete " one of the "

Col. 8, line 48    Delete " one of the "

Col. 8, line 61    Delete " one of the "

Signed and Sealed this

Seventh Day of November, 1995

Attest:

BRUCE LEHMAN

*Attesting Officer*    *Commissioner of Patents and Trademarks*